United States Patent [19]

Lindel et al.

[11] Patent Number: 4,920,136
[45] Date of Patent: Apr. 24, 1990

[54] SUBSTITUTED PYRIDYLETHANOLAMINE LIVESTOCK PRODUCTION PROMOTERS

[75] Inventors: Hans Lindel, Leverkusen; Werner Hallenbach, Langenfeld; Friedrich Berschauer, Wuppertal, all of Fed. Rep. of Germany

[73] Assignee: Bayer Aktiengesellschaft, Leverkusen, Fed. Rep. of Germany

[21] Appl. No.: 218,740

[22] Filed: Jul. 13, 1988

[30] Foreign Application Priority Data

Jul. 29, 1987 [DE] Fed. Rep. of Germany ....... 3725084

[51] Int. Cl.$^5$ ............... A61K 31/44; C07D 213/84; C07D 413/00
[52] U.S. Cl. ............... 514/344; 514/235.5; 514/318; 514/343; 514/352; 514/355; 514/356; 514/338; 514/124; 514/131; 546/193; 546/194; 546/281; 546/289; 546/270; 546/304; 546/309; 546/310; 546/312; 546/316; 546/318; 546/286
[58] Field of Search ............... 546/289, 304, 309, 310, 546/312, 311, 270, 316, 318, 286; 514/344, 338, 355, 356

[56] References Cited

FOREIGN PATENT DOCUMENTS

| 0049728 | 4/1982 | European Pat. Off. ............ 546/304 |
| 0209025 | 1/1987 | European Pat. Off. ............ 546/304 |
| 0225600 | 6/1987 | European Pat. Off. ............ 546/304 |
| 0244728 | 11/1987 | European Pat. Off. ............ 546/304 |

Primary Examiner—Mary C. Lee
Assistant Examiner—J. Richter
Attorney, Agent, or Firm—Sprung Horn Kramer & Woods

[57] ABSTRACT

For promoting livestock production, the novel substituted pyridylethanolamines of the formula

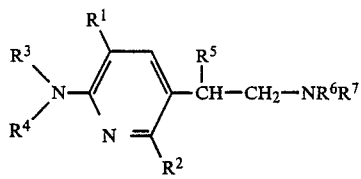

in which
- $R^1$ represents CN, —COOR$^8$ or —CONR$^9$R$^{10}$,
- $R^2$ represents optionally substituted alkyl,
- $R^3$ represents hydrogen, alkyl or alkenyl,
- $R^4$ represents hydrogen or optionally substituted alkyl or alkenyl, or
- $R^3$ and $R^4$ represent, together with the nitrogen atom to which they are bonded, an optionally substituted heterocyclic radical,
- $R^5$ represents OH, acyloxy or alkoxy,
- $R^6$ represents hydrogen or alkyl,
- $R^7$ represents hydrogen, alkyl, cycloalkyl, substituted alkyl, optionally substituted aralkyl, aryl or heterocyclyl,
- $R^6$ and $R^7$ can, together with the nitrogen atom to which they are bonded, represent an optionally substituted heterocyclic radical,
- $R^8$ represents alkyl, and
- $R^9$ and $R^{10}$, independently of one another, represent hydrogen, alkyl or alkenyl or, together with the nitrogen atom to which they are bonded, represent an optionally substituted heterocyclic radical, or a physiologically tolerated salt or N-oxide thereof. Some intermediates are also new.

13 Claims, No Drawings

SUBSTITUTED PYRIDYLETHANOLAMINE LIVESTOCK PRODUCTION PROMOTERS

The present invention relates to substituted pyridylethanolamines, processes for their preparation, intermediates for carrying out these processes, and their use as production promoters in livestock.

The use of feedstuff additives to achieve higher weight gains and improved feed conversion is practiced in livestock nutrition, in particular in fattening pigs, cattle and poultry.

Heteroarylethylamines have already been disclosed. The compounds have beta-sympathomimetic effects (DE-OS (German Published Specification) 2,603,600, EP-OS (European Published Specification) 120,770, U.S. patent specification No. 4,358,455). However, nothing is known about their suitability as production promoters in livestock.

The following have been found:

1. New substituted pyridylethanolamines of the formula I

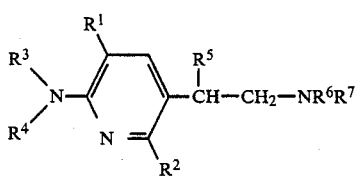

in which
R$^1$ represents CN, —COOR$^8$ or —CONR$^9$R$^{10}$,
R$^2$ represents optionally substituted alkyl,
R$^3$ represents hydrogen, alkyl or alkenyl,
R$^4$ represents hydrogen or optionally substituted alkyl or alkenyl, or
R$^3$ and R$^4$ represent, together with the nitrogen atom to which they are bonded, an optionally substituted heterocyclic radical,
R$^5$ represents OH, acyloxy or alkoxy,
R$^6$ represents hydrogen or alkyl,
R$^7$ represents hydrogen, alkyl, cycloalkyl, substituted alkyl, optionally substituted aralkyl, aryl or heterocyclyl, or
R$^6$ and R$^7$ can, together with the nitrogen atom to which they are bonded, represent an optionally substituted heterocyclic radical,
R$^8$ represents alkyl, and
R$^9$ and R$^{10}$, independently of one another, represent hydrogen, alkyl or alkenyl or, together with the nitrogen atom to which they are bonded, represent an optionally substituted heterocyclic radical,
and their physiologically tolerated salts and their N-oxides.

2. Process for the preparation of the substituted pyridylethanolamines of the formula I

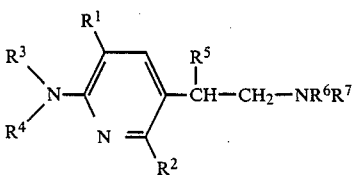

in which
R$^1$ represents CN, —COOR$^8$ or —CONR$^9$R$^{10}$,
R$^2$ represents optionally substituted alkyl,
R$^3$ represents hydrogen, alkyl or alkenyl,
R$^4$ represents hydrogen or optionally substituted alkyl or alkenyl, or
R$^3$ and R$^4$ represent, together with the nitrogen atom to which they are bonded, an optionally substituted heterocyclic radical,
R$^5$ represents OH, acyloxy or alkoxy,
R$^6$ represents hydrogen or alkyl,
R$^7$ represents hydrogen, alkyl, cycloalkyl, substituted alkyl, optionally substituted aralkyl, aryl or heterocyclyl, or
R$^6$ and R$^7$ can, together with the nitrogen atom to which they are bonded, represent an optionally substituted heterocyclic radical,
R$^8$ represents alkyl, and
R$^9$ and R$^{10}$, independently of one another, represent hydrogen, alkyl or alkenyl or, together with the nitrogen atom to which they are bonded, represent an optionally substituted heterocyclic radical,
characterized in that substituted pyridyl halogenomethyl ketones of the formula II

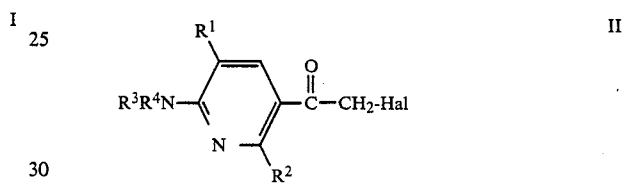

in which
R$^1$, R$^2$, R$^3$ and R$^4$ have the abovementioned meanings, and
Hal represents halogen,
are reacted with amines of the formula III

HNR$^6$R$^7$   III in which
R$^6$ and R$^7$ have the abovementioned meaning,
and then the carbonyl group is reduced and thereafter, where appropriate, acylated or alkylated.

3. Substituted pyridyl halogenomethyl ketones of the formula II

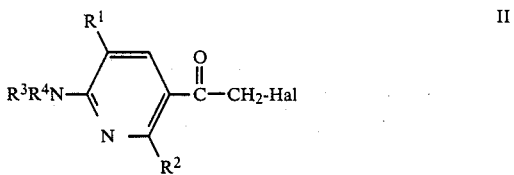

in which
R$^1$ represents CN, —COOR$^8$ or —CONR$^9$R$^{10}$,
R$^2$ represents optionally substituted alkyl,
R$^3$ represents hydrogen, alkyl or alkenyl,
R$^4$ represents hydrogen or optionally substituted alkyl or alkenyl, or
R$^3$ and R$^4$ represent, together with the nitrogen atoms to which they are bonded, an optionally substituted heterocyclic radical,
R$^8$ represents alkyl,
R$^9$ and R$^{10}$, independently of one another, represent hydrogen, alkyl or alkenyl or, together with the nitrogen atom to which they are bonded, represent an optionally substituted heterocyclic radical, and Hal represents halogen.

4. Process for the preparation of the pyridyl halogenomethyl ketones of the formula II

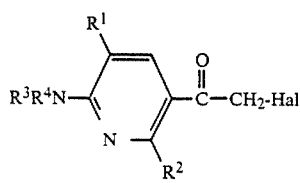
II in which
R¹, R², R³, R⁴ and Hal have the meaning indicated under 3,
characterized in that substituted pyridyl methyl ketones of the formula IV

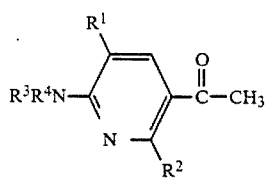
IV in which
R¹, R², R³ and R⁴ have the abovementioned meaning, are halogenated.

5. Substituted pyridyl methyl ketones of the formula IV

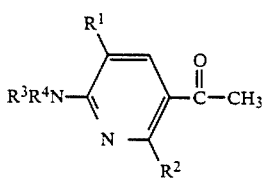
IV in which
R¹ represents CN, —COOR⁸ or —CONR⁹R¹⁰,
R² represents optionally substituted alkyl,
R³ represents hydrogen, alkyl or alkenyl,
R⁴ represents hydrogen or optionally substituted alkyl or alkenyl, or
R³ and R⁴ represent, together with the nitrogen atoms to which they are bonded, an optionally substituted heterocyclic radical,
R⁸ represents alkyl, and
R⁹ and R¹⁰, independently of one another, represent hydrogen, alkyl or alkenyl or, together with the nitrogen atom to which they are bonded, represent an optionally substituted heterocyclic radical.

6. Process for the preparation of the substituted pyridyl methyl ketones of the formula IV

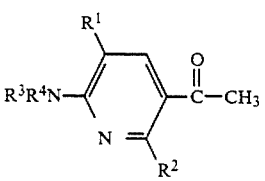
IV in which
R¹, R², R³ and R⁴ have the meaning indicated under 5, characterized in that pyridyl methyl ketones of the formula V

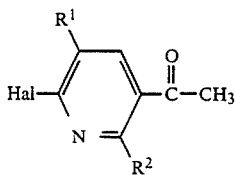
V in which
R¹ and R² have the abovementioned meaning, and
Hal represents halogen,
are reacted with amines of the formula VI

H—NR³R⁴     VI in which
R³ and R⁴ have the abovementioned meaning.

7. Pyridyl-methyl ketones of the formula V

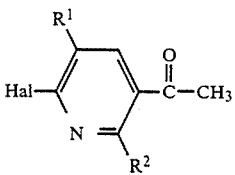
V in which
R¹ represents CN, —COOR⁸ or —CONR⁹R¹⁰,
R² represents optionally substituted alkyl, and
R⁸ represents alkyl, and
R⁹ and R¹⁰, independently of one another, represent hydrogen, alkyl or alkenyl or, together with the nitrogen atom to which they are bonded, represent an optionally substituted heterocyclic radical,
Hal represents halogen.

8. Process for the preparation of the pyridyl methyl ketones of the formula V

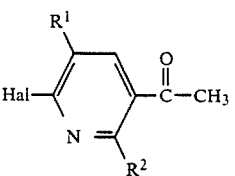
V in which
R¹, R² and Hal have the meanings indicated under V,
characterized in that compounds of the formula VII

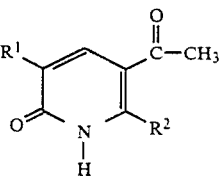
VII in which
R¹ and R² have the abovementioned meaning, are reacted with phosphorus oxychloride, where appropriate in the presence of acid-binding agents.

The compounds of the formula I can exist in the form of their tautomers. Examples of these are:

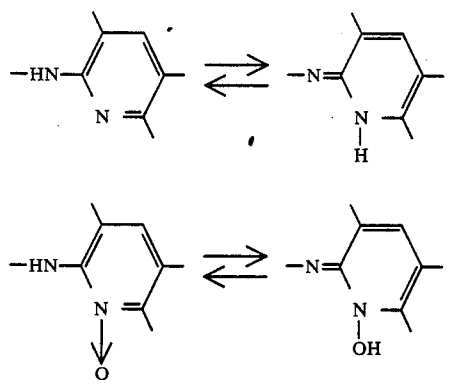

The compounds of the formula I can also exist in the form of their racemates or enantiomeric forms.

Physiologically tolerated salts of the compounds of the formula I can be formed with the following acids: hydrochloric acid, sulphuric acid, phosphoric acid, perchloric acid, hydrobromic or hydriodic acid, nitric acid, acetic acid, oxalic acid, malonic acid, succinic acid, ascorbic acid, malic acid, tartaric acid, maleic acid, fumaric acid, methanesulphonic acid, benzoic acid, substituted benzoic acid, formic acid, toluenesulphonic acid, benzenesulphonic acid, phthalic acid, naphthalenesulphonic acid, nicotinic acid, palmitic acid and embonic acid.

Preferred compounds of the formula I are those in which $R^1$ represents CN,
$R^2$ represents $C_{1-4}$-alkyl,
$R^3$ represents hydrogen or $C_{1-4}$-alkyl,
$R^4$ represents hydrogen or $C_{1-4}$-alkyl, or
$R^3$ and $R^4$, together with the nitrogen atom to which they are bonded, represent an optionally substituted 5- to 6-membered saturated or unsaturated heterocyclic radical, which can contain N or O as further heteroatoms,
$R^5$ represents OH, $C_{1-6}$-alkoxy or acyloxy, and acyloxy represents oxycarbonyl-$C_{1-6}$-alkyl, optionally substituted oxycarbonylphenyl, oxysulphonyl-$C_{1-6}$-alkyl, or optionally substituted oxysulphonylphenyl,
$R^6$ represents hydrogen or $C_{1-6}$-alkyl,
$R^7$ represents hydrogen, optionally substituted $C_{1-6}$-alkyl, $C_{3-6}$-cycloalkyl, $C_{1-6}$-alkylphenyl or phenyl, or
$R^6$ and $R^7$ can, together with the nitrogen atom to which they are bonded, represent an optionally substituted 5- to 6-membered saturated or unsaturated heterocyclic radical which can optionally also contain further heteroatoms from the series comprising N, O and S,
$R^8$ represents $C_{1-6}$-alkyl, and
$R^9$ and $R^{10}$, independently of one another, represent hydrogen or $C_{1-4}$-alkyl.

Particularly preferred compounds of the formula I are those in which $R^1$ represents CN,
$R^2$ represents methyl or ethyl,
$R^3$ represents hydrogen, methyl or ethyl,
$R^4$ represents hydrogen, methyl or ethyl, or
$R^3$ and $R^4$, together with the nitrogen atom to which they are bonded, represent a heterocycle from the series comprising pyrrolidine, pyrrole, piperidine and morpholine, each of which can optionally be substituted by halogen or $C_{1-4}$-alkyl,
$R^5$ represents OH or $C_{1-6}$-alkoxy, in particular methoxy or ethoxy,
$R^6$ represents hydrogen or $C_{1-4}$-alkyl, in particular methyl or ethyl, and
$R^7$ represents hydrogen, $C_{1-6}$-alkyl which is optionally substituted by 1 to 5 halogen atoms, in particular methyl, ethyl, propyl, butyl, pentyl or hexyl, particular mention being made of secondary and tertiary alkyl radicals, as well as $C_{1-6}$-alkylphenyl which can optionally be substituted by halogen, in particular fluorine or chlorine, $C_{1-4}$-alkyl, hydroxyl, $C_{1-4}$-alkoxy, or optionally halogen-substituted methylenedioxy or ethylenedioxy; $C_{1-6}$-alkylphenoxy which can optionally be substituted by halogen, in particular fluorine or chlorine, $C_{1-4}$-alkyl, hydroxyl, $C_{1-4}$-alkoxy, or optionally halogen-substituted methylenedioxy or ethylenedioxy.

The following specific compounds of the formula I may be mentioned:

| $R^1$ | $R^2$ | $R^3$ | $R^4$ | $R^5$ | $R^6$ | $R^7$ |
|---|---|---|---|---|---|---|
| C≡N | CH$_3$ | H | H | OH | H | −CH(CH$_3$)−C$_6$H$_5$ |
| C≡N | CH$_3$ | H | H | OH | —CH$_2$—CH$_2$—O—CH$_2$—CH$_2$— | |
| C≡N | CH$_3$ | H | H | OH | H | −CH(CH$_3$)−CH$_2$−CH$_2$−C$_6$H$_5$ |
| C≡N | CH$_3$ | H | H | OH | H | −CH$_2$−CH(CH$_3$)$_2$ |
| C≡N | CH$_3$ | H | H | OH | H | −CH(CH$_3$)−CH$_2$−OCH$_3$ |
| C≡N | CH$_3$ | H | H | OH | H | −CH(Et)−CH$_3$ |
| C≡N | CH$_3$ | H | H | OH | —(CH$_2$)$_5$— | |

-continued

| R¹ | R² | R³ | R⁴ | R⁵ | R⁶ | R⁷ |
|---|---|---|---|---|---|---|
| C≡N | CH₃ | H | H | OH | H | cyclopropyl |
| C≡N | CH₃ | H | H | OH | H | cyclohexyl (H) |
| C≡N | CH₃ | H | H | OH | H | cyclopentyl |
| C≡N | CH₃ | H | H | OH | H | indanyl |
| C≡N | CH₃ | H | H | OH | H | Adamantyl |
| C≡N | CH₃ | CH₃ | H | OH | H | —CH(CH₃)₂ |
| C≡N | CH₃ | CH₃ | CH₃ | OH | H | —CH(CH₃)₂ |
| C≡N | CH₃ | —(CH₂)₄— | | OH | H | —CH(CH₃)₂ |
| C≡N | —Et | H | H | OH | H | —CH(CH₃)₂ |
| —C(=O)N(CH₃)CH₃ | CH₃ | CH₃ | CH₃ | OH | H | —CH(CH₃)₂ |
| —C(=O)NH₂ | CH₂ | H | H | OH | H | —CH(CH₃)₂ |

Salts which may be mentioned as preferred are those with hydrochloric acid, sulphuric acid, phosphoric acid, oxalic acid, maleic acid, fumaric acid and malonic acid.

The new compounds of the formula I can be prepared by the abovementioned process 2.

When, in process 2, 2-methyl-3-chloroacetyl-5-cyano-6-amino-pyridine is used as halogenomethyl ketone of the formula II, and t-butylamine is used as amine of the formula III, process 2 can be represented by the following reaction diagram:

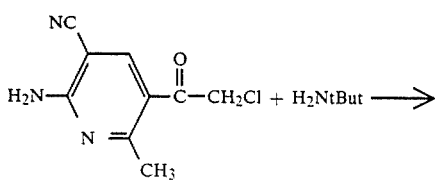

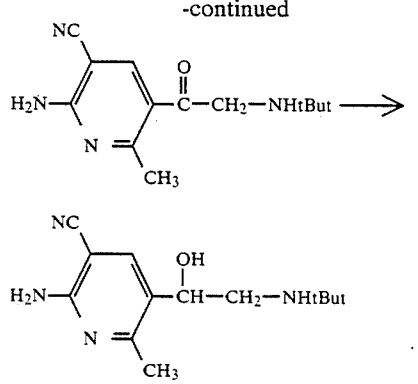

The compounds of the formula II are new. They are prepared by the processes described hereinafter. Preferred compounds of the formula II are those in which the substituents R¹, R², R³ and R⁴ have the preferred meanings indicated for compounds of the formula I, and Hal represents chlorine or bromine.

The following specific pyridyl halogenomethyl ketones of the formula II may be mentioned:

$$\underset{R^3R^4N}{\overset{R^1}{\diagdown}}\underset{N}{\overset{}{\bigcirc}}\underset{R^2}{\overset{\overset{O}{\|}}{C-CH_2-Hal}}$$

| $R^1$ | $R^2$ | $R^3$ | $R^4$ | Hal |
|---|---|---|---|---|
| C≡N | CH₃ | H | H | Br |
| C≡N | CH₃ | CH₃ | H | Br |
| C≡N | CH₃ | CH₃ | CH₃ | Br |
| C≡N | CH₃ | —(CH₂)₄— | | Br |
| —C(=O)OCH₃ | CH₃ | H | H | Br |
| —C(=O)N(CH₃)CH₃ | CH₃ | CH₃ | CH₃ | Br |
| —C(=O)NH₂ | CH₃ | H | H | Br |

The amines of the formula III are known or can be prepared in analogy to known processes. The substituents $R^6$ and $R^7$ preferably have the meanings indicated hereinbefore as preferred for the compounds of the formula I. The following specific compounds of the formula III may be mentioned:

Ammonia, methylamine, dimethylamine, ethylamin, diethylamine, methylethylamine, n-propylamine, i-propylamine, n-butylamine, i-butylamine, tert.-butylamine, cyclopentylamine, cyclohexylamine, benzylamine, aniline, piperidine, pyrrolidine, morpholine and 2-aminopyridine.

The following reducing agents may be mentioned as reducing agents for carrying out the process: H₂/catalyst, examples of catalysts which may be mentioned are: PtO₂, Pd/active charcoal; complex metal hydrides such as, for example, LiAlH₄, NaBH₄ and NaBH₃CN.

The following reducing agents are particularly preferably used: NaBH₄ and NaBH₃CN.

The process is carried out by mixing the compounds of the formula II and III in approximately equivalent ratio in a diluent.

The reaction is preferably carried out at temperatures from −20° C. to +100° C.

It is preferably carried out under atmospheric pressure.

All inert organic solvents are used as diluents. These include, in particular, aliphatic and aromatic hydrocarbons such as pentane, hexane, cyclohexane, petroleum ether, ligroin, benzene and toluene; chlorinated hydrocarbons such as methylene chloride, ethylene chloride and chloroform; ethers, such as diethyl ether and glycol dimethyl ether; nitriles such as acetonitrile, propionitrile and benzonitrile; alcohols, such as methanol, ethanol, n- and i-propanol.

Alcohols are preferred, it being possible to carry out the reduction immediately without isolating the intermediates.

As already mentioned, the pyridyl halogenomethyl ketones of the formula II are new. They are prepared by the process indicated under 3. This can be represented by the following equation with 2-ethyl-3-acetyl-5-carbethoxy-6-methylamino-pyridine and elemental bromine:

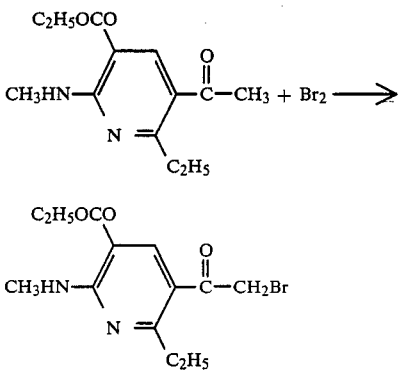

The substituted pyridyl methyl ketones of the formula IV used for carrying out process 3 are new. They are prepared by the process described hereinafter.

Preferred substituted pyridyl methyl ketones of the formula IV are those in which $R^1$, $R^2$, $R^3$ and $R^4$ have the meanings mentioned as preferred for the compounds of the formula I.

The following specific compounds of the formula IV may be mentioned:

$$\underset{R^3R^4N}{\overset{R^1}{\diagdown}}\underset{N}{\overset{}{\bigcirc}}\underset{R^2}{\overset{\overset{O}{\|}}{C-CH_3}}$$

| $R^1$ | $R^2$ | $R^3$ | $R^4$ |
|---|---|---|---|
| C≡N | CH₃ | H | H |
| C≡N | CH₃ | CH₃ | H |
| C≡N | CH₃ | CH₃ | CH₃ |
| C≡N | CH₃ | —(CH₂)₄— | |
| C≡N | Et | H | H |
| —C(=O)OCH₃ | CH₃ | H | H |
| —C(=O)N(CH₃)CH₃ | CH₃ | CH₃ | CH₃ |
| —C(=O)NH₂ | CH₃ | H | H |

The halogenation in process 3 is carried out with suitable halogenating agents, where appropriate at elevated temperature and in the presence of diluents.

Halogenating agents which may be mentioned are: elemental halogen, in particular bromine, copper(II) halides, in particular CuBr$_2$, and sulphuryl chloride. The halogenating agents are generally used in an amount which is approximately stoichiometric to that of the compounds of the formula IV. An up to 5-fold, preferably up to 1.5-fold, excess of halogenating agent may be advantageous.

The halogenation is carried out between $-10°$ and $+150°$ C., preferably between $0°$ and $100°$ C. It is also preferred to carry it out at the boiling point of the diluent.

It is preferably carried out under atmospheric pressure. Suitable diluents are optionally substituted aliphatic or aromatic hydrocarbons such as pentane, hexane, heptane, cyclohexane, petroleum spirit, benzene, ligroin, petroleum ether and toluene, methylene chloride, ethylene chloride, chloroform, carbon tetrachloride, chlorobenzene and o-dichlorobenzene. Alcohols, such as methanol and ethanol, esters such as ethyl acetate, and glacial acetic acid may also be mentioned for carrying out the halogenation with bromine or CuBr$_2$.

The halogenation with bromine is preferably carried out in the presence of equimolar amounts of hydrobromic acid.

After the reaction is complete, the reaction mixture is worked up in a manner known per se.

As already mentioned, the pyridyl methyl ketones of the formula IV are new. They are prepared by the process indicated under 5. This can be represented by the following equation with 2-methyl-3-acetyl-5-cyano-6-chloro-pyridine and pyrrole as starting compounds of the formulae V and VI:

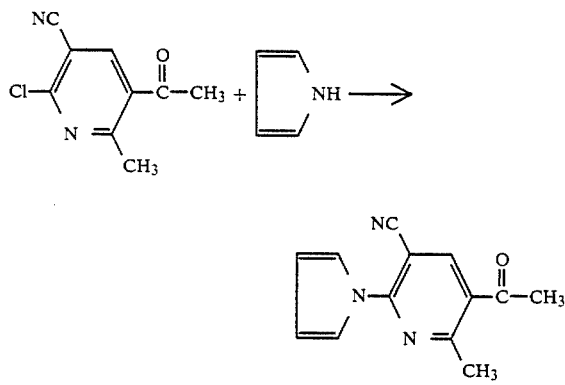

The compounds of the formula V used for carrying out process 5 are new. They are prepared by the process described hereinafter. The compounds of the formula VI are known. Preferred compounds of the formulae V and VI are those in which the substituents $R^1$, $R^2$, $R^3$ and $R^4$ have the preferred meanings indicated for compounds of the formula I, and Hal in compound V represents Cl.

The following specific compounds of the formula V may be mentioned:

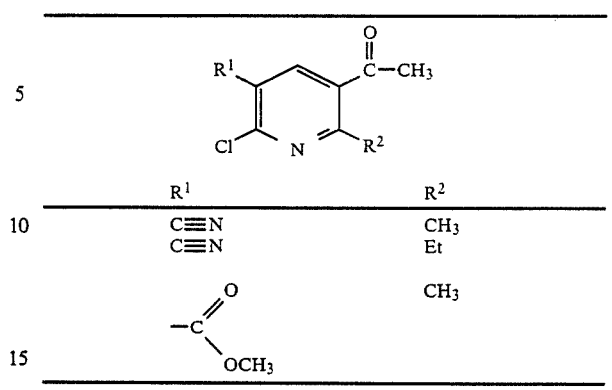

| $R^1$ | $R^2$ |
|---|---|
| C≡N | CH$_3$ |
| C≡N | Et |
| −C(=O)OCH$_3$ | CH$_3$ |

The following specific amines of the formula III may be mentioned:

Ammonia, methylamine, dimethylamine, ethylamine, diethylamine, methylethylamine, n-propylamine, i-propylamine, n-butylamine, i-butylamine, tert.-butylamine, cyclopentylamine, cyclohexylamine, piperidine, pyrrolidine, pyrrole and morpholine.

The reaction is carried out at temperatures of $0°$ C. to $200°$ C., preferably at $25°$ to $125°$ C.

It is preferably carried out under atmospheric pressure. Where the reaction is carried out with volatile amines such as, for example, ammonia, it is preferably carried out under pressure.

All inert organic solvents serve as diluents. These include, in particular, aliphatic and aromatic, optionally halogenated, hydrocarbons, such as pentane, hexane, heptane, cyclohexane, petroleum ether, petroleum spirit, ligroin, benzene, toluene, methylene chloride, ethylene chloride, chloroform, carbon tetrachloride, chlorobenzene and o-dichlorobenzene, as well as ethers such as diethyl and dibutyl ether, glycol dimethyl ether and diglycol dimethyl ether, tetrahydrofuran and dioxane, nitriles such as, for example, acetonitrile, propionitrile, benzonitrile and glutaronitrile, furthermore amides such as, for example, dimethylformamide, dimethylacetamide and N-methylpyrrolidone, as well as tetramethylene sulphone and hexamethylphosphoric triamide, furthermore alcohols such as methanol, ethanol, n- and i-propanol. The reaction can also be carried out without diluent.

The reaction can be carried out in the presence of auxiliary bases such as tertiary organic amines, for example triethylamine, tripropylamine, tributylamine, N,N-dimethylaniline and pyridine.

The amines of the formula VI are preferably used in excess (2 to 10 mols of amine per mol compound of the formula V). When an auxiliary base is used, the excess of the amine of the formula V can be reduced to 1 to 3 mols of amine, preferably 1 to 1.5 mols of amine, per mol of compound of the formula V. In this case, 1 to 3 mols of auxiliary base, preferably 1 to 1.5 mols of auxiliary base, is used per mol of compound of the formula V.

The reaction mixture is worked up in a manner known per se.

As already mentioned, the compounds of the formula V are new. They are prepared by the process indicated under VII. This can be represented by the following equation with 2-methyl-3-acetyl-5-cyano-6-pyridone as compound of the formula VII and phosphorus oxychloride as starting compounds:

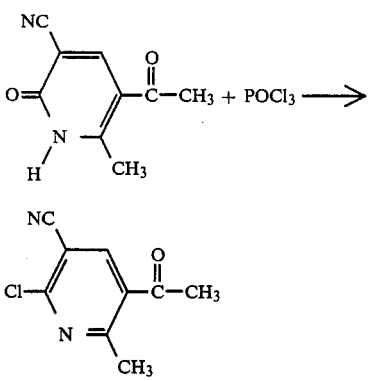

The compounds of the formula VII used for carrying out process 8 are known or can be prepared in analogy to known processes (P. Schenone et al. J. Heterocycl. Chem. 22, page 1503 (1985); L. Crombie et al., J. Chem. Soc. Perkin Trans 1, pages 677–685 (1979).

Preferred compounds of the formula VII are those in which the substituents $R^1$ and $R^2$ have the preferred meanings indicated for the compounds of the formula I.

The following specific compound of the formula VII may be mentioned:

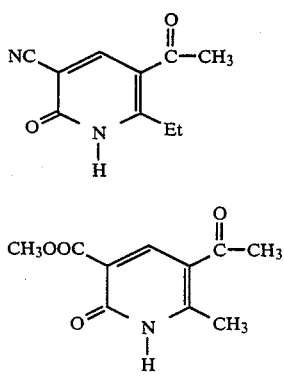

The reaction is carried out by treating a compound of the formula VII with 1 to 5 mols, preferably 1 to 1.5 mols, of the inorganic acid chloride, where appropriate in a diluent.

The reaction is carried out at temperatures from 50° C. to 150° C., and preferably under atmospheric pressure.

The reaction can be carried out in the presence of acid-binding agents. Those which may be mentioned as preferred are tertiary organic amines such as, for example, triethylamine, tripropylamine, tributylamine, N,N-dimethylaniline and pyridine.

All inert organic solvents can be used as diluents. These include, in particular, aliphatic and aromatic, optionally halogenated hydrocarbons such as pentane, hexane, cyclohexane, benzene, toluene, methylene chloride, chloroform and chlorobenzene; ethers such as diethyl ether, tetrahydrofuran and dioxane, and nitriles and esters.

The reaction is preferably carried out without diluent.

The working up is carried out in a manner known per se by hydrolysis of the halogenating agent and filtering off the reaction product with suction of distilling off the solvent.

The active compounds have a favorable toxicity to warm-blooded species and are suitable as agents for promoting the production of breeding and productive livestock. In this context, they act to promote the speed up growth, and the production of milk and wool, and to improve the feed conversion and the quality of meat and to shift the meat/fat ratio in favor of meat.

The productive and breeding livestock include mammals such as, for example, cattle, horses, sheep, pigs, goats, camels, water buffalo, donkeys, rabbits, fallow deer, reindeer, fur-bearing livestock such as, for example, mink, chinchilla and racoon, birds such as, for example, chickens, geese, turkeys and ducks, and fresh- and salt-water fish such as, for example, trout, carp and eels.

The active compounds are used, irrespective of the sex of the livestock, during all phases of growth and production of the livestock. The active compounds are preferably used during the intensive phases of growth and production. The intensive phases of growth and production last, depending on the species, from one month up to 10 years. The active compounds prove to be particularly valuable in the rearing and management of young and fattening livestock.

The active compounds are administered enterally or parenterally, directly or in the form of formulations suitable for livestock. Enteral administration of the active compounds takes place, for example, orally in the form of powders, tablets, capsules, pastes, drenches, granules, boli, via solutions, emulsions or suspensions which can be administered orally, as well as via the feed or via the drinking water. Parenteral administration takes place, for example, in the form of injection (intramuscular, subcutaneous, intravenous or by implants).

Formulations for administration via the feed or the drinking water may be particularly emphasised. In this context, the active compounds can be added to the feed directly or in the form of premixes or feed concentrates.

The feed includes single feedstuffs of plant origin such as hay, roots, cereals and cereals by-products, molasses and silage, single feedstuffs of animal origin such as meat, fats, milk products and bonemeal, fish products and the single feedstuffs such as vitamins, proteins, sugars, starch, meals, amino acids for example DL-methionine, and salts such as lime and sodium chloride. The feed also includes supplementary, mixed and compounded feed-stuffs. These contain single feedstuffs in a composition which ensures a balanced diet in terms of the energy and protein supply and of the supply of vitamins, mineral salts and trace elements.

Premixes and feed concentrates are mixtures of the active compound with vehicles and, where appropriate, other auxiliaries. The vehicles include all the single feedstuffs or mixtures thereof.

The active compounds can be present in the formulations alone or mixed with other production-promoting active compounds, mineral feedstuffs, trace element compounds, vitamins, nitrogen-containing non-protein compounds, colorants, antioxidants, flavorings, emulsifiers, free-flow agents, preservatives and pellet binders.

Examples of other production-promoting active compounds are antibiotics such as tylosine and virginiamycin Examples of mineral feedstuffs are dicalcium phosphate, magnesium oxide and sodium chloride. Examples of trace element compounds are iron fumarate, sodium iodide, cobalt chloride, copper sulphate, zinc oxide and selenium compounds. Examples of vitamins are vitamin A, vitamin $D_3$ and vitamin E.

Examples of nitrogen-containing non-protein compounds are biuret and urea. Examples of colorants are carotenoids such as canthaxanthin, zeaxanthin, capsanthin or colorants approved for coloring foodstuffs. Examples of antioxidants are ethoxyquin, butylated hydroxy-toluene and ascorbic acid. Examples of flavorings are vanillin. Examples of emulsifiers are esters of lactic acid, and lecithin. Examples of free-flow agents are sodium stearate, calcium stearate, silicic acid, bentonite and ligninsulphonates.

Examples of preservatives are propionic acid, calcium propionate, sorbic acid and ascorbic acid. Examples of pellet binders are ligninsulphonates and cellulose ethers.

The concentration of the active compounds in the feed is normally about 0.001-500 ppm, preferably 0.1-50 ppm.

The concentration of the active compounds in the premixes or feed concentrates is about 0.5 to 50 per cent by weight, preferably 1 to 20 per cent by weight.

The amount of the active compounds which is administered to the livestock to achieve the desired effect can be varied widely because of the favourable properties of the active compounds. It is preferably about 0.001 to 50 mg/kg, in particular 0.01 to 5 mg/kg, of body weight per day. The appropriate amount of the active compound, and the appropriate duration of administration, depend in particular on the species, the age, the sex, the state of health and the type of management and feeding of the livestock and can readily be determined by all those skilled in the art.

The active compounds are administered to the livestock by the customary methods. The nature of administration depends in particular on the species, the behavior and the state of health of the livestock. The active compounds can be administered once. However, it is also possible to administer the active compounds temporarily or continuously during the whole or during a part of the phases of growth and production. In the case of continuous administration, the administration can take place once or several times a day, at regular or irregular intervals.

Example for the composition of a chick rearing feed which contains active compound according to the invention:

200 g of wheat, 340 g of corn, 361 g of soy meal, 60 g of beef tallow, 15 g of dicalcium phosphate, 10 g of calcium carbonate, 4 g of iodized sodium chloride, 7.5 g of vitamin/mineral mixture of the composition indicated below, and 2.5 g of active compound premix of the composition indicated below, provide, after careful mixing, 1 kg of feed.

1 kg of vitamin/mineral mixture contains: 600 I.U. of vitamin A, 100 I.U. of vitamin $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times H_2O$, 100 mg of $FeSO_4 \times 7 H_2O$ and 20 mg of $CuSO_4 \times 5 H_2O$ in cereal meal as vehicle.

1 kg of active compound premix contains 100 g of active compound and 900 g of wheat meal.

Example for the composition of a pig rearing feed which contains active compound according to the invention: 630 g of feed cereal meal (composed of 200 g of corn, 150 g of barley meal, 150 g of oat meal and 130 g of wheat meal), 80 g of fish meal, 60 g of soy meal, 60 g of cassava meal, 38 g of brewer's yeast, 50 g of vitamin/mineral mixture (composition as for chicken feed), 30 g of linseed cake meal, 30 g of corn gluten feed, 10 g of soy oil, 10 g of sugarcane molasses and 2 g of active compound premix provide, after careful mixing, 1 kg of feed. 1 kg of active compound premix contains 200 g of active compound, 20 g of vegetable oil and 780 g of calcium carbonate powder.

Example for the composition of a feed for cattle which contains the active compound according to the invention:

69.95% feed cereal meal, 10% milled corncobs, 8% soy bean meal, 5% lucerne meal, 5% molasses, 0.6% urea, 0.5% calcium phosphate, 0.5% calcium carbonate, 0.3% sodium chloride, 0.15% vitamin/mineral mixture and 0.2% active compound premix of the composition indicated for pig rearing feed. The vitamin/mineral mixture contains per kg 70,000 i.U. of vitamin A, 70,000 i.U. of vitamin $D_3$, 100 mg of vitamin E, 50 mg of $MnSO_4 \times H_2O$ and 30 mg of $ZnSO_4 \times 7 H_2O$ in cereal meal as vehicle.

The active compound premix is admixed to the vitamin/mineral mixture in the required amount, and the latter is then carefully mixed with the other constituents.

EXAMPLE

Rat-feeding trial

Female laboratory Wistar rats of the SPF type and weighing 90-110 g (bred by Hagemann) are fed ad lib with standard rat feed to which the desired amount of active compound has been added. Each trial series is carried out with feed from the same batch so that differences in the composition of the feed cannot impair the comparability of the results.

The rats receive water ad lib.

Each trial group is formed of 12 rats which are fed with feed to which the desired amount of active compound has been added. A control group receives feed without active compound. The composition of the trial groups is such that the mean body weight and the variation in the body weights of the rats in each trial group is the same, so that comparability between the trial groups is ensured.

Before the start of the trial, the animals are acclimatized to the new housing conditions for 2 days, during which feed without added active compound is provided. Thereafter the animals receive feed containing the active compound for 13 days. The relative weight gain, related to the untreated controls, is determined.

The results shown in the table are obtained:

TABLE

| Rat feeding trial Active compound Example No. | Active compound concentration ppm | Relative weight gain |
| --- | --- | --- |
| 1 | 25 | 127 |
| 4 | 25 | 119 |
| 6 | 5 | 122 |
| 7 | 5 | 116 |

PREPARATION EXAMPLES

EXAMPLE 1

2-N-Isopropylamino-1-(6-amino-5-cyano-2-methyl-3-pyridyl)ethanol 830 mg (14 mmol) of isopropylamine are introduced into 50 ml of methanol, and then 1.2 g (4.7 mmol) of 2-amino-5-bromoacetyl-3-cyano-6-methyl-pyridine are introduced. The mixture is heated to 50° C. and stirred at this temperature for two hours. The suspension is then cooled to 0° C., and 400 mg (10.5 mmol) of NaBH₄ are added.

The reaction is complete after one hour at 0° C. For the working up, the mixture is evaporated in vacuo, and the residue is partitioned between water and ethyl acetate. The organic phase is separated off, the product is extracted into a 5% strength NaH₂PO₄ solution, and the organic phase is discarded. The aqueous phase is made alkaline with NaOH and is extracted with CHCl₃. Drying with Na₂SO₄ is followed by evaporation and, for purification, recrystallization from ethyl acetate.

Yield: 465.8 mg (42% of theory).
Melting point: 158° C.

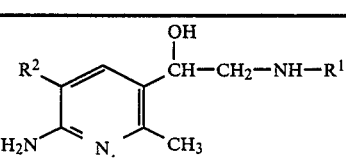

| Example No. | R¹ | R² | Melting point |
|---|---|---|---|
| 2 | tert.-Butyl | C≡N | 136° C. |
| 3 | -CH(CH₃)-CH₂-phenyl | C≡N | 132° C. |
| 4 | tert.-Butyl | -C(=O)OCH₃ | 148° C. |
| 5 | -CH(CH₃)-phenyl | C≡N | 170° C. Diastereomer A<br>147° C. Diastereomer B |
| 6 | -CH(CH₃)CH₂-CH₂-phenyl | C≡N | IR: 3400–3200 (broad), 2950, 2200, 1665, 1605, 1495, 1450, 1365, 735, 685 cm⁻¹ |
| 7 | -CH₂-CH(CH₃)₂ | C≡N | 163° C. |
| 8 | -CH(CH₃)-CH₂OCH₃ | C≡N | 136° C. |
| 9 | -CH(CH₃)-Et | C≡N | 139° C. |
| 10 | cyclohexyl-H | C≡N | 149° C. |
| 11 | cyclopentyl | C≡N | 170° C. |
| 12 | (structure: N≡C-, H₂N-, pyridine with CH(OH)-CH₂-N-piperidine, CH₃) | | 144° C. |

EXAMPLE 13
EXAMPLE FOR PROCESS 4

2-Amino-5-bromoacetyl-3-cyano-6-methyl-pyridine 2.7 g (15.4 mmol) of 5-acetyl-2-amino-3-cyano-6-methyl-pyridine are suspended in 110 ml of glacial acetic acid, and 1.9 ml (16.2 mmol) of 48% strength HBr are added. Then 5.2 g (32.4 mmol) of bromine are added, and the mixture is stirred at 45° C. for five hours. After cooling, the mixture is filtered with suction and the filter cake is stirred with NaHCO₃ solution, filtered with suction and dried. Recrystallization from ethanol is used for purification.

Yield: 2.3 g (59% of theory).
Melting point: 209° C. (decomposition).

EXAMPLE 14
EXAMPLE FOR PROCESS 6

3-Acetyl-5-cyano-2-methyl-6-morpholino-pyridine 9.5 g (48.8 mmol) of 3-acetyl-6-chloro-5-cyano-2-methyl-pyridine are dissolved in 180 ml of toluene, 9.5 g (0.109 mol) of morpholine are added, and the mixture is stirred at 90° C. for two hours. To work up, the mixture is evaporated, and the residue is suspended in water, filtered with suction and carefully washed with water. Re-crystallization from methanol/water is used for purification.

Yield: 11.1 g (92.8% of theory).
Melting point: 126° C.
Further examples for process 6

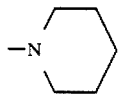

| Example No. | R | Melting point: |
|---|---|---|
| 15 | —NH-i-C₃H₇ | 105° C. |
| 16 |  | 91° C. |
| 17 | 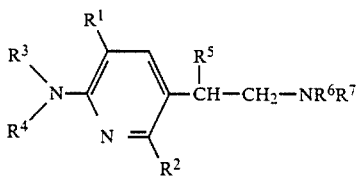 | 134° C. |

The following are obtained analogously:

EXAMPLE 18

3-Acetyl-5-cyano-2-methyl-6-methylaminopyridine
Melting point: 239° C.

EXAMPLE FOR PROCESS 6

EXAMPLE 19

5-Acetyl-2-amino-3-cyano-6-methyl-pyridine 40 g (0.21 mol) of 5-acetyl-2-chloro-3-cyano-6-methyl-pyridine are dissolved in 800 ml of tetrahydrofuran, 200 ml of concentrated aqueous NH₃ solution are added, and the mixture is heated at 80° C. in a stirred autoclave for two hours. After cooling, the mixture is concentrated and filtered, and the filter cake is extracted by boiling in acetonitrile and is filtered with suction.

Yield: 27.2 g (75.5% of theory).
Melting point: 219° C., yellow plates.

EXAMPLE FOR PROCESS 8

EXAMPLE 20

3-Acetyl-5-cyano-6-chloro-2-methyl-pyridine 35 g (0.2 mol) of 5-acetyl-3-cyano-6-methyl-2-pyridone* are suspended in 400 ml of chlorobenzene, 24.2 g (0.2 mol) of N,N-dimethylaniline are added, and 37 g (0.24 mol) of POCl₃ are added dropwise. The mixture is then heated at 100° C. for three hours. After cooling, the mixture is cautiously poured onto water, neutralization with dilute sodium hydroxide solution is carried out, the organic phase is separated off, and the aqueous phase is again extracted with CHCl₃. The combined extracts are dried with Na₂SO₄ and evaporated. The residue is purified by filtration through silica gel, using CH₂Cl₂/ethyl acetate as eluent.

*Preparation L. Mosti, P. Schenone and G. Menozzi, J. Heterocycl. Chem. 22, 1503 (1985).

Yield: 26.7 g (68.5% of theory).
Melting point: 98° C.

It will be appreciated that the instant specification and claims are set forth by way of illustration and not limitation, and that various modifications and changes may be made without departing from the spirit and scope of the present invention.

What is claimed is:

1. A substituted pyridylethanolamine derivative of the formula in which
$R^1$ represents CN, COOR⁸ or CONR⁹R¹⁰
$R^2$ represents $C_{1-4}$-alkyl,
$R^3$ represents hydrogen or $C_{1-4}$-alkyl,
$R^4$ represents hydrogen or $C_{1-4}$-alkyl,
$R^5$ represents OH, $C_{1-6}$-alkoxy, $C_1$–$C_6$-alkylcarbonyloxy, phenylcarbonyloxy, $C_1$–$C_6$-alkylsulphonyloxy, or phenylsulphonyloxy,
$R^6$ represents hydrogen or $C_{1-6}$-alkyl,
$R^7$ represents hydrogen, $C_{1-6}$-alkyl, $C_{3-6}$-cycloalkyl, $C_{1-6}$-alkylphenyl or phenyl each of which is optionally substituted by 1 to 5 halogen atoms, $C_{1-6}$-alkylphenyl which can optionally be substituted by halogen, $C_{1-4}$-alkyl, hydroxyl, $C_{1-4}$-alkoxy, or optionally halogen-substituted methylenedioxy or ethylenedioxy; $C_{1-6}$-alkyl-phenoxy which can optionally be substituted by halogen, $C_{1-4}$-alkyl, hydroxyl, $C_{1-4}$-alkoxy, or optionally halogen-substituted methylenedioxy or ethylenedioxy,
$R^8$ represents $C_{1-6}$-alkyl, and
$R^9$ and $R^{10}$, independently of one another, represent hydrogen or $C_{1-4}$-alkyl.

2. A substituted pyridyl methyl ketone of the formula

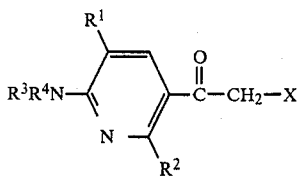

in which

R$^1$ represents CN, —COOR$^8$ or —CONR$^9$R$^{10}$,

R$^2$ represents C$_1$–C$_4$-alkyl,

R$^3$ represents hydrogen or C$_{1-4}$-alkyl,

R$^4$ represents hydrogen or C$_{1-4}$-alkyl,

R$^8$ represents C$_{1-6}$-alkyl,

R$^9$ and R$^{10}$, independently of one another, represent hydrogen or C$_{1-4}$ alkyl, and X represents halogen or hydrogen.

3. A pyridyl methyl ketone of the formula

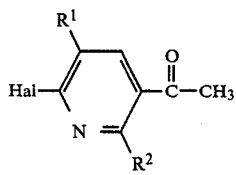

in which

R$^1$ represents CN, —COOR$^8$— or —CONR$^9$R$^{10}$,

R$^2$ represents C$_{1-4}$-alkyl,

R$^8$ represents C$_{1-6}$-alkyl,

R$^9$ and R$^{10}$, independently of one another, represent hydrogen or C$_{1-4}$-alkyl, and Hal represents halogen.

4. A compound, salt of N-oxide according to claim 1, in which

R$^1$ represents CN,

R$^2$ represents methyl,

R$^5$ represents OH,

R$^6$ represents hydrogen, and

R$^7$ represents C$_{1-6}$-alkyl substituted by C$_{1-4}$-alkoxy.

5. A compound, salt or N-oxide according to claim 1, in which

R$^1$ represents CN,

R$^2$ represents methyl or ethyl,

R$^3$ represents hydrogen, methyl or ethyl,

R$^4$ represents hydrogen, methyl or ethyl,

R$^5$ represents OH or C$_{1-6}$-alkoxy, and

R$^6$ represents hydrogen or C$_{1-4}$-alkyl.

6. A compound according to claim 1, wherein such compound is 2-N-isopropylamino-1-(6-amino-5-cyano-2-methyl-3-pyridyl)-ethanol of the formula

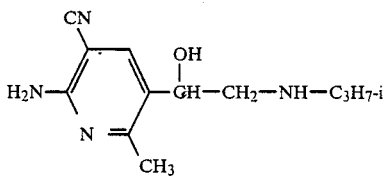

or a physiologically tolerated salt or N-oxide thereof.

7. A compound according to claim 1, wherein such compound is 2-N-tert.-butylamino-1-(6-amino-5-carbomethoxy-2-methyl-3-pyridyl)-ethanol of the formula

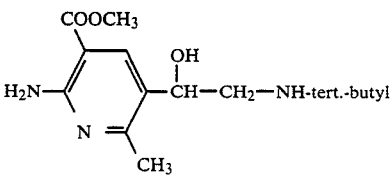

or a physiologically tolerated salt or N-oxide thereof.

8. A compound according to claim 1, wherein such compound is 2-(N-phenyl-1-methyl-propyl-amino)-1-(6-amino-5-cyano-2-methyl-3-pyridyl)-ethanol of the formula

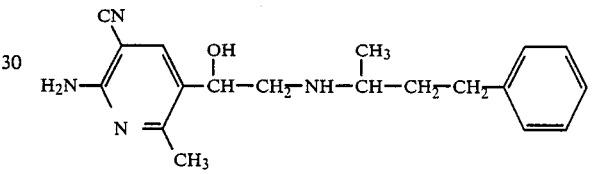

or a physiologically tolerated salt or N-oxide thereof.

9. A compound according to claim 1, wherein such compound is 2-N-sec.-butylamino-1-(6-amino-5-cyano-2-methyl-3-pyridyl)-ethanol of the formula

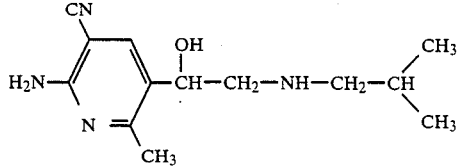

or a physiologically tolerated salt or N-oxide thereof.

10. A livestock promoting composition comprising an amount effective therefor of a compound, salt or N-oxide according to claim 1 and a diluent.

11. A composition according to claim 10 wherein the diluent is an animal feed base.

12. A method of promoting livestock production which comprises administering to such livestock an amount effective therefor of a compound, salt or N-oxide according to claim 1.

13. The method according to claim 12, wherein such compound is
2-N-isopropylamino-1-(6-amino-5-cyano-2-methyl-3-pyridyl)-ethanol,
2-N-tert.-butylamino-1-(6-amino-5-carbomethoxy-2-methyl-3-pyridyl)-ethanol,
2-(N-phenyl-1-methyl-propyl-amino)-1-(6-amino-5-2-methyl-3-pyridyl)-ethanol, or
2-N-sec.-butylamino-1-(6-amino-5-cyano-2-methyl-3-pyridyl)-ethanol,
or a physiologically tolerated salt or N-oxide thereof.

* * * * *